United States Patent [19]

Jürgen et al.

[11] Patent Number: 5,104,875

[45] Date of Patent: Apr. 14, 1992

[54] COMBINATION PREPARATIONS CONTAINING RIFAMPICIN AND THIOACETAZON

[75] Inventors: Klaus Jürgen; Joachim Seydel, both of Borstel, Fed. Rep. of Germany

[73] Assignee: Fatol Arzneimittel GmbH, Schiffweiler, Fed. Rep. of Germany

[21] Appl. No.: 523,243

[22] Filed: May 15, 1990

[30] Foreign Application Priority Data

May 19, 1989 [DE] Fed. Rep. of Germany ....... 3916417

[51] Int. Cl.$^5$ .................. A61K 35/50; A61K 31/495; A61K 31/175

[52] U.S. Cl. .................................. 514/253; 514/254; 514/582

[58] Field of Search .................. 514/253, 254, 582

[56] References Cited

U.S. PATENT DOCUMENTS 3,751,567  8/1973  Konopka et al. .................. 424/114

OTHER PUBLICATIONS

The Merck Index, Ninth Edition, Merck & Co., Inc., Rahway, N.J., 1976, p. 1198.

Primary Examiner—Jerome D. Goldberg
Attorney, Agent, or Firm—Nixon & Vanderhye

[57] ABSTRACT

Pharmaceutical combination preparations containing rifampicin and thioacetazon and optionally isonicotinic acid hydrazide or ethambutol and the use of same for the treatment of mycobacterial infections.

7 Claims, No Drawings

COMBINATION PREPARATIONS CONTAINING RIFAMPICIN AND THIOACETAZON

The invention relates to combination preparations, which contain rifampicin and thioacetazon, and optionally in addition isonicotinic acid hydrazide or ethambutol, as active agents. The combination preparations according to the invention have proved extraordinarily effective in the treatment of mycobacterial diseases. The preparations display therapeutic activity in particular against mycobacteria of the MOTT complex (mycobacteria other than tuberculosis) and of these in particular against the group of avian mycobacteria.

The spectrum of mycobacterial diseases extends from "classical" tuberculosis caused by *Mycobacterium tuberculosis* through leprosy to the infections caused by so-called atypical or "non-tuberculosis" mycobacteria. The latter are frequently grouped together under the name "MOTT-complex". Although these types are less virulent and pathogenic than *M. tuberculosis* or *M. leprae*; however, they gain increasing significance for patients with weakened immune systems. This is true primarily for patients with AIDS and senile tuberculosis, but also occurs after organ transplantation, and an increase has been observed quite generally in infections with atypical mycobacteria.

In the case of AIDS-patients, infections with mycobacteria of the MOTT-complex, and in particular with *M.avium*, are frequently at least partly responsible for the lethal outcome of the illness (cf. Aerztliche Praxis 13, 370 (1989)).

In this context, it has proved fatal that hitherto no really effective therapy has been available for the opportunistic infections caused by atypical mycobacteria.

It is therefore an object of the invention to provide preparations which can be used to combat effectively infections caused by mycobacteria, and in particular the mycobacteria of the MOTT-complex, such as *M. avium*.

According to the invention it has surprisingly emerged that using combination preparations containing rifampicin (RMP) and thioacetazon (Thz), both the growth and the multiplication of the typical mycobacteria, *M. tuberculosis* and *M. leprae*, and also that of the atypical mycobacteria of the MOTT-complex and in particular *M. avium*, can be inhibited to an extraordinarily great extent. Accordingly, a therapeutic effect takes place such as cannot be achieved by the individual components of the combination preparation according to the invention in therapeutically justifiable doses.

Although RMP is currently the most effective agent against mycobacteria, it has no effect or only a slight effect against the mycobacteria of the MOTT-complex when administered alone (cf. Example 2, Table 2 and Table 5). Furthermore, strains of *M. tuberculosis* and *M. leprae* are continually appearing which are either primarily resistant to RMP, or have acquired resistance through selection under monotherapy.

The anti-mycobacterial effect of Thz has likewise been known for a long time. It is, however, only of weak effect when administered alone in acceptable doses and can lead to undesirable side-effects in higher doses.

Unexpectedly, it has now emerged that the combination of RMP and Thz has a far greater than average synergistic effect against mycobacteria and in particular against *M. avium*. While, for example, the average inhibiting concentration of Thz alone against a *M. avium* strain isolated from an AIDS patient (*M. avium* 227, cf. Example 2) is 32 µg/ml and that of rifampicin is 8 µg/ml, only 0.36 µg/ml of each of the two components in combination is required to inhibit completely the multiplication of the bacterial cells (cf. Table 3). This is therefore not an additive effect, but a genuine and very highly marked synergistic effect. This result is all the more surprising in view of the fact that in anti-mycobacterial therapy the "full-dose principle" is assumed, i.e. the individual components are only expected to be effective in combination when the full individually effective dose is used.

According to a particularly preferred embodiment of the invention, the combination preparations additionally contain isonicotinic acid hydrazide (INH) or ethambutol (EMB). According to the invention, it has surprisingly emerged that in the presence of INH or EMB the doses of RMP and Thz required for a successful inhibition of the target organisms once again decrease markedly (cf. Example 5, Table 5). The total active-agent quantity can therefore be reduced considerably still further by including INH or EMB.

The combination preparations according to the invention, due to the nature of the diseases for which they are considered, must generally be administered over relatively long periods of time, i.e. frequently about 12 to 24 months. Since the therapeutic effect only takes place when both substances are applied simultaneously, it must be ensured that the combination is taken regularly and in the prescribed amounts. This cannot, however, be ensured in a prolonged treatment with the individual substances.

The combination preparations according to the invention are therefore preferably available as fixed combinations, in which the ratio of the active agents RMP to Thz is preferably (2 to 6) :(0.5 to 2). In the presence of INH or EMB as an additional active agent in the combination preparation according to the invention, the ratio of RMP to Thz to INH is preferably (2 to 6) :(0.5 to 2) : (1 to 4) and the ratio of RMP to Thz to EMB is preferably (2 to 6) : (0.5 to 2) : (6 to 16).

It is particularly preferred for the preparation to exist in a form suitable for oral administration, i.e. as tablets, dragees or capsules. Such dosage units preferably contain 300 to 700 mg RMP and 50 to 100 mg Thz, and, in a particularly preferred embodiment, 400 mg RMP and 75 mg Thz. If INH or EMB are also present in the formulation, then dosage units are preferred which contain 100 to 300 mg RMP, 25 to 75 mg Thz and 50 to 200 mg INH or 400 to 700 mg EMB.

The tablets can be produced in the usual manner by incorporation of the conventional excipients, substrates and auxiliary agents.

The invention is further demonstrated by means of the following Examples.

EXAMPLE 1

Isolation of M.avium from Patient Sera

Strains of *mycobacterium avium* were isolated from the sera of four different patients according to known processes ("Isolierung von Mykobakterien", DIN 58943, Part 3, 1980)).

The symptoms of each of the patients and the designation of the isolate are presented below in Table 1.

TABLE 1

| Clinical picture | Designation of isolate |
|---|---|
| atypical mycobacteriosis in AIDS | M. avium 227 |
| atypical mycobacteriosis | M. avium Ro |
| " | M. avium Dan |
| " | M. avium Bi |

EXAMPLE 2

Determination of the Minimum Inhibiting Concentration (MIC) of the Individual Substances The MIC of the individual substances RMP and Thz was determined according to known standard processes ("Methoden zur Empfindlichkeitsprüfung von bakteriellen Krankheitserregern", DIN 58940, Part 5) against the M. avium strains as in Example 1.

The bacteria were cultivated in a liquid nutrient medium according to Lockemann (cf. "Nachweisverfahren für Mykobakterien aus Untersuchungsmaterial, III, Nährbodenrezepte zur Kultur von Tuberkulosebakterien, 1978, Publisher: Deutsches Zentralkomitee zur Bekämpfung der Tuberkulose, Poppenhusenstrasse 14c, 2000 Hamburg 60) enriched with 0.5 % albumin and 1 % human serum. In each case $5 \times 10^{-3}$ to $5 \times 10^{-5}$ mg, referred to the weight in wet state, of the mycobacteria strains were incubated in 2 ml of the culture liquid at 37° C. with graded concentrations of RMP and Thz. Readings were taken from the culture tubes after 8 to 15 days.

The MIC is the concentration of the growth inhibitor in µg/ml, at which no multiplication of the seeded cells can be established.

The results are reproduced in Table 2. They show that M. avium Ro is completely resistant to both substances, while M. avium Dan is resistant to Thz and 16 µg/ml of RMP alone are required to inhibit growth completely. For the other strains tested, the corresponding amount for RMP is between 3 and 8 µg/l and the amount for Thz is between 3 and 32 µg/l. Also these strains are, however, not susceptible to therapy by the individual substances because the serum concentrations necessary are not achievable by dosis amounts conventional and clinically acceptable.

TABLE 2

| | MIC µg/ml | |
|---|---|---|
| Strain | RMP | Thz |
| M. avium 227 | 8 | 32 |
| M. avium Ro | >32 | >32 |
| M. avium Dan | 16 | >32 |
| M. avium Bi | 3 | 3 |

EXAMPLE 3

The MIC values for the combinations according to the invention for the strains in Example 1 were determined by dilution series with a constant ratio of the active agents.

The bacteria were incubated under the conditions in Example 2.

The sum of the fractional inhibiting concentration (FII) was calculated according to the equation of C. W. Norden et al., J. Infect.-Dis. 140, 290 (1978):

$$FII = \frac{MIC \text{ of compound } A \text{ in combination}}{MIC \text{ of compound } A \text{ alone}} + \frac{MIC \text{ of compound } B \text{ in combination}}{MIC \text{ of compound } B \text{ alone}}$$

When FII<1 there is synergism, while FII>>1 signifies antagonism.

The results are indicated in Table 3. They show that in all cases FII values were obtained which were far below 1. The active agents RMP and Thz in combination accordingly have an extremely synergistic effect on the tested strains.

TABLE 3

| Strain | MIC µg/ml (comb.) RMP/Thz | FII |
|---|---|---|
| M. avium 227 | 0.36/0.36 | 0.056 |
| M. avium Ro | 0.32/0.32 | <0.01 |
| M. avium Dan | 0.24/0.24 | <0.022 |
| M. avium Bi | a. 0.22/0.22 | 0.146 |
| | b. 0.18/0.18 | 0.120 |

EXAMPLE 4

The MIC values of the combination of RMP and Thz according to the invention were determined by "chessboard" titrations (cf. Berenbaum, N.C., J. Infekt. Dis. 137, 122 to 130, 1978 and J. K. Seydel et al., Chemotherapie 29, 249 (1983)) against the strain M.tuberculosis H37Rv and against the RMP-resistant patient strain M. avium BK. Results of the cheesboard titrations are reported as:

+++ = growth as control
++ = slight growth inhibition
+ = marked growth inhibition
(+) = almost complete growth inhibition
− = complete growth inhibition.

The results are indicated in Tables 4a and 4b. They show that the synergistic activity of the combination is also developed against these strains.

EXAMPLE 5

The experiments as in Examples 2 and 3 were repeated, and the MIC values of the active agents RMP, Thz, INH and EMB alone and in the combinations RMP/Thz, RMP/Thz/INH and RMP/Thz/EMB according to the invention were determined against 10 further mycobacteria of the avium complex isolated from different patients.

The results are indicated in Table 5. They show the synergistic activity of the combinations according to the invention, an extreme increase in the synergistic effect being achieved in each case by incorporating INH or EMB.

| Example 6 | | | |
|---|---|---|---|
| Tablets were prepared from the following components according to conventional methods: | a) mg | b) mg | c) mg |
| rifampicin | 400 | 300 | 300 |
| thioacetazon | 75 | 75 | 75 |
| isonicotinic acid hydrazide | — | 175 | — |
| ethambutol | — | — | 400 |
| cellulose powder | 188 | 163 | 335 |
| carboxymethyl-cellulose-Na, cross-linked | 30 | 30 | 50 |
| SiO$_2$ | 8 | 8 | 10 |
| talcum | 16 | 16 | 20 |
| polyvinylpyrrolidone | 8 | 8 | 10 |

-continued

Example 6

| Tablets were prepared from the following components according to conventional methods: | a) mg | b) mg | c) mg |
|---|---|---|---|
| total amount | 725 | 775 | 1200 |

TABLE 4

| | | Thioacetazon | | | | | | | | | |
|---|---|---|---|---|---|---|---|---|---|---|---|
| ug/ml | | .50 | .45 | .40 | .35 | .30 | .25 | .20 | .15 | .10 | .05 | 0 |
| Rifampicin | .06 | | | | | | | | | | | − |
| | .054 | | | | | | | | | | | − |
| | .048 | | | | | | | | | | | + |
| | .042 | | | | | | | | | | | + |
| | .036 | | | | | | | | | | | + |
| | .030 | | | | | | | | | | | ++ |
| | .024 | | | | | | | | | | | +++ |
| | .018 | | | | | | | | | | + | +++ |
| | .012 | | | | | | | | | | ++ | +++ |
| | .006 | | | | | | | | | + | ++ | +++ |
| | 0 | +++ | +++ | +++ | +++ | +++ | +++ | +++ | +++ | +++ | +++ | +++ |

| strain: | H37Rv M. tub. |
|---|---|
| medium: | Lockemann + 0,5 Albumin + 1% H-Serum |
| inoculation: | $1.91 \times 10^{-1}$ |

| | | Rifampicin | | | | | | | | | |
|---|---|---|---|---|---|---|---|---|---|---|---|
| ug/ml | | 8 | 7.2 | 6.4 | 5.4 | 4.8 | 4 | 3.2 | 2.4 | 1.6 | 0.8 | 0 |
| Thioacetazon | 8 | | | | | | | | | | | + |
| | 7.2 | | | | | | | | | | | + |
| | 6.4 | | | | | | | | | | | + |
| | 5.6 | | | | | | | | | | | + |
| | 4.8 | | | | | | | | | | | ++ |
| | 4 | | | | | | | | | | | ++ |
| | 3.2 | | | | | | | | | | | ++ |
| | 2.4 | | | | | | | | | | | ++ |
| | 1.6 | | | | | | | | | | | +++ |
| | 0.8 | | | | | | | | | | | +++ |
| | 0.000 | − | − | − | − | − | − | ++ | ++ | +++ | +++ | +++ |

| strain: | M. avium Bk. |
|---|---|
| medium: | Lockemann + 0,5% Albumin + 1% H-Serum |
| inoculation: | $1.91 \times 10^{-1}$ |

TABLE 5

| Patient's Code Administration Form | Substance | Sa | Me | Ku | Wi | Vo | Bi | Ma | Ka-B | LB | LA |
|---|---|---|---|---|---|---|---|---|---|---|---|
| | | | | | | M I C (ug/ml) | | | | | |
| single | RMP | 8 | 16 | 32 | >32 | 16 | 4 | >32 | >32 | 32 | >32 |
| " | Thz | 32 | 32 | 32 | 32 | 32 | >32 | >32 | >32 | 32 | 16 |
| " | INH | 32 | 16 | 4 | 16 | 8 | >32 | >32 | >32 | 16 | 4 |
| " | EMB | >32 | 8 | >32 | >32 | 4–8 | 4 | 32 | >32 | 16–32 | >32 |
| in combination | RMP/ | 4 | 8 | 2 | 4 | 8 | — | 1 | 8 | ≧8 | 2 |
| | Thz | 1 | 2 | 0.5 | 1 | 2 | — | 0.25 | 2 | ≧2 | 0.5 |
| " | RMP/ | 4 | 2 | 0.5 | 2 | 4 | 1 | 2 | 4 | 4 | 2 |
| | Thz/ | 1 | 0.5 | 0.12 | 0.5 | 1 | 0.25 | 1 | 1 | 1 | 1 |
| | INH | 2 | 1 | 0.25 | 1 | 2 | 0.5 | 0.5 | 2 | 2 | 0.5 |
| " | RMP/ | 1 | 1 | 1 | 1 | 4 | — | 1 | 8 | 8 | 2 |
| | Thz/ | 0.5 | 0.5 | 0.5 | 0.5 | 1 | — | 0.5 | 2 | 2 | 0.5 |
| | EMB | 1 | 1 | 1 | 1 | 2 | — | 1 | 4 | 4 | 4 |

What is claimed is:

1. A pharmaceutical combination in orally administrable form for the treatment of mycobacterial infections consisting essentially of effective amounts of rifampicin and thioacetazon as the active ingredients in a synergistic weight ratio of rifampicin to thioacetazon of 2 to 6:0.5 to 2.

2. The pharmaceutical combination of claim 1, containing from about 300 to about 700 mg rifampicin and from about 50 to about 100 thioacetazon.

3. The pharmaceutical combination of claim 2, containing about 400 mg rifampicin and about 75 mg thioacetazon.

4. A pharmaceutical composition in orally administrable form for the treatment of mycobacterial infections consisting essentially of effective amounts of rifampicin and thioacetazon as the active ingredients in a synergistic weight ratio of rifampicin to thioacetazon of 2 to 6:0.5 to 2; together with a pharmaceutically acceptable carrier.

5. A method treating a mycobacterial infection comprising orally administering to a patient having same, an effective amount, in combination, of rifampicin and thioacetazon as the active ingredients in a synergistic weight ratio of rifampicin to thioacetazon of 2 to 6:0.5 to 2.

6. The method of claim 5, in which the infection is caused by a mycobacteria of the MOTT complex.

7. The method of claim 5, in which the infection is caused by a mycobacteria of the avium species.

* * * * *

UNITED STATES PATENT AND TRADEMARK OFFICE
CERTIFICATE OF CORRECTION

PATENT NO. : 5,104,875
DATED : April 14, 1992
INVENTOR(S) : Klaus Jurgen SCHAPER et al It is certified that error appears in the above-identified patent and that said Letters Patent is hereby corrected as shown below:

On the Title page, under item [19], "Jurgen" should be --Schaper--; and

Item [75], "Klaus Jurgen" should be --Klaus Jurgen Schaper--.

Signed and Sealed this

Thirty-first Day of August, 1993

Attest:

BRUCE LEHMAN

Attesting Officer	Commissioner of Patents and Trademarks